US006841197B2

United States Patent

(12) United States Patent
Standke et al.
(10) Patent No.: US 6,841,197 B2
(45) Date of Patent: Jan. 11, 2005

(54) N-PROPYLETHOXYSILOXANES, THEIR PREPARATION AND USE

(75) Inventors: Burkhard Standke, Loerrach (DE); Helmut Mack, Rheinfelden (DE)

(73) Assignee: Degussa AG, Duesseldorf (DE)

( * ) Notice: Subject to any disclaimer, the term of this patent is extended or adjusted under 35 U.S.C. 154(b) by 245 days.

(21) Appl. No.: 09/987,268

(22) Filed: Nov. 14, 2001

(65) Prior Publication Data

US 2002/0090316 A1 Jul. 11, 2002

(30) Foreign Application Priority Data

Nov. 14, 2000 (DE) ........................................ 100 56 344

(51) Int. Cl.[7] .................................................. B05D 3/02

(52) U.S. Cl. ...................... 427/387; 252/8.62; 428/447; 428/405; 428/428; 525/477; 524/379; 524/837

(58) Field of Search ........................ 427/387; 252/8.62; 524/379, 837; 528/12; 428/405, 428, 447

(56) References Cited

U.S. PATENT DOCUMENTS

| | | | | |
|---|---|---|---|---|
| 3,354,022 A | | 11/1967 | Dettre et al. | |
| 3,772,065 A | | 11/1973 | Seiler | |
| 4,604,443 A | * | 8/1986 | Chang et al. | 528/28 |
| 4,716,051 A | | 12/1987 | Rödder | |
| 5,112,393 A | | 5/1992 | Engel et al. | |
| 5,225,510 A | * | 7/1993 | Bank et al. | 528/12 |
| 5,282,998 A | * | 2/1994 | Horn et al. | 252/182.14 |
| 5,527,937 A | | 6/1996 | Standke et al. | |
| 5,536,860 A | | 7/1996 | Monkiewicz et al. | |
| 5,543,173 A | | 8/1996 | Horn, Jr. et al. | |
| 5,629,400 A | | 5/1997 | Standke et al. | |
| 5,646,325 A | | 7/1997 | Monkiewicz et al. | |
| 5,679,147 A | | 10/1997 | Standke et al. | |
| 5,808,125 A | | 9/1998 | Standke et al. | |
| 5,849,942 A | | 12/1998 | Standke et al. | |
| 5,863,509 A | | 1/1999 | Standke et al. | |
| 5,885,341 A | | 3/1999 | Standke et al. | |
| 5,932,757 A | | 8/1999 | Standke et al. | |
| 6,084,116 A | | 7/2000 | Horn et al. | |
| 6,177,582 B1 | | 1/2001 | Jenkner et al. | |
| 6,177,584 B1 | | 1/2001 | Loewenberg et al. | |
| 6,228,936 B1 | | 5/2001 | Standke et al. | |
| 6,239,194 B1 | | 5/2001 | Standke et al. | |
| 6,251,989 B1 | | 6/2001 | Edelmann et al. | |
| 6,255,516 B1 | | 7/2001 | Jenkner et al. | |
| 6,288,256 B1 | | 9/2001 | Standke et al. | |
| 6,361,871 B1 | | 3/2002 | Jenkner et al. | |
| 6,395,858 B1 | | 5/2002 | Mack et al. | |
| 6,403,228 B1 | | 6/2002 | Mack et al. | |
| 6,491,838 B1 | | 12/2002 | Standke et al. | |
| 6,500,883 B1 | | 12/2002 | Mack et al. | |
| 6,528,585 B1 | | 3/2003 | Standke et al. | |
| 6,534,667 B1 | | 3/2003 | Standke et al. | |
| 2003/0018155 A1 | * | 1/2003 | Krafcyzk | 528/10 |

FOREIGN PATENT DOCUMENTS

| | | |
|---|---|---|
| DE | 1 518 551 | 2/1969 |
| DE | 27 44 726 | 4/1979 |
| DE | 28 09 871 | 9/1979 |
| DE | 198 18 923 | 11/1999 |
| DE | 198 23 390 | 12/1999 |
| DE | 198 34 990 | 4/2000 |
| DE | 198 49 308 | 5/2000 |
| DE | 199 04 132 | 8/2000 |
| DE | 199 08 636 | 8/2000 |
| DE | 199 55 047 | 6/2001 |
| EP | 0 101 816 | 3/1984 |
| EP | 0 538 555 | 4/1993 |
| EP | 0 579 453 | 1/1994 |
| EP | 0 587 667 | 3/1994 |
| EP | 0 590 270 | 4/1994 |
| EP | 0 716 127 | 6/1996 |
| EP | 0 716 128 | 6/1996 |
| EP | 0 761 675 | 3/1997 |
| EP | 0 814 110 | 12/1997 |
| EP | 0 832 911 | 4/1998 |
| EP | 0 846 715 | 6/1998 |
| EP | 0 846 716 | 6/1998 |
| EP | 0 846 717 | 6/1998 |
| EP | 0 879 842 | 11/1998 |
| EP | 0 885 895 | 12/1998 |
| EP | 0 930 342 | 7/1999 |
| WO | WO 92/06101 | 4/1992 |
| WO | WO 95/23830 | 9/1995 |

OTHER PUBLICATIONS

Derwent Abstract, EP 0 748 357, (with corr. WO 95/23830).

J. K. Crandall, et al., Journal of Organometallic Chemistry, vol. 489, pp. 5–13, "Siloxanes from the Hydrolysis of Isopropyltrimethoxysilane", 1995.

Patent Abstracts of Japan, JP 03–040976, Feb. 21, 1991.

* cited by examiner

*Primary Examiner*—Margaret G. Moore
*Assistant Examiner*—Marc S Zimmer
(74) *Attorney, Agent, or Firm*—Oblon, Spivak, McClelland, Maier & Neustadt, P.C.

(57) ABSTRACT

An oligomer mixture of n-propylethoxysiloxanes, containing from 80 to 100% by weight of n-propylethoxysiloxanes having a degree of oligomerization ranging from 2 to 6.

36 Claims, 1 Drawing Sheet

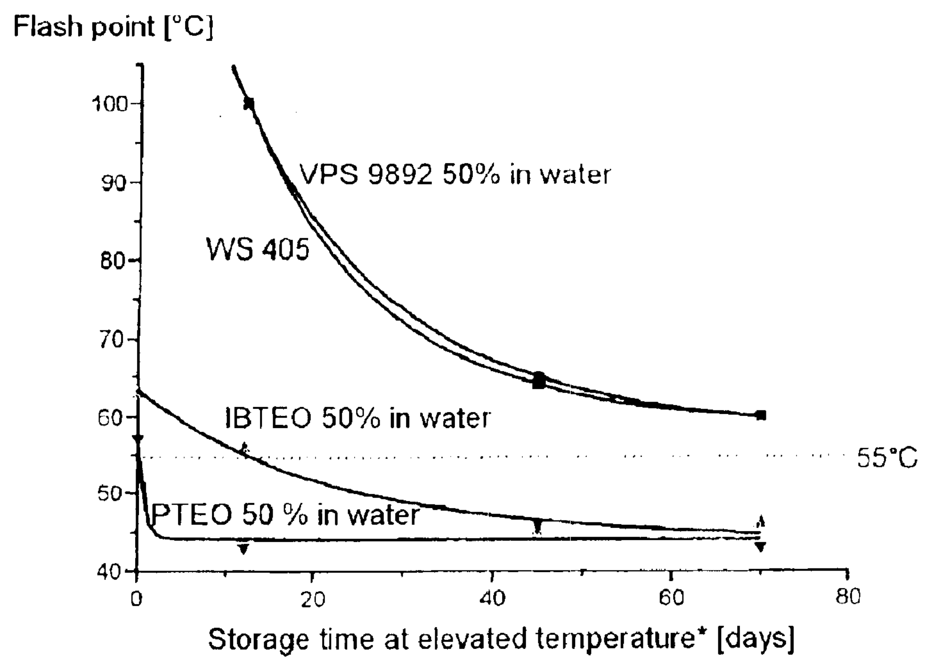
Fig. 1: Flash point of various emulsions as a function of the storage time (*storage temperature approx. 50 ± 10°C)

N-PROPYLETHOXYSILOXANES, THEIR PREPARATION AND USE

BACKGROUND OF THE INVENTION

1. Field of the Invention

The present invention relates to specific mixtures of n-propylethoxysiloxanes, to a process for preparing them, and to their use.

2. Description of the Background

Alkyl-functional silanes and siloxanes are employed, for example, in the hydrophobicization of absorbent mineral materials.

EP 0 814 110 A1 describes the preparation of catenated and/or cyclic $C_3$–$C_{18}$ alkylalkoxysiloxanes by a two-stage process starting from the corresponding alkyl chlorosilane, which is first esterified to the alkylalkoxysilane and then, secondly, the ester product undergoes controlled hydrolysis and condensation to give the desired alkylalkoxysiloxane product. In this process, more than 1 mol of water per mole of Si is employed for the controlled hydrolysis and condensation. Alkylalkoxysiloxanes obtained in this manner are generally in the form of a mixture of oligomers. Besides alkyl and alkoxy groups, the alkylalkoxysiloxanes may also carry hydroxyl groups, if alcohol is eliminated from the siloxane by hydrolysis. Otherwise, siloxanes, as disclosed in EP 0 814 110 A1, possess a degree of oligomerization, n ranging from 2 to 20, i.e., they have 2 to 20 Si units per molecule, possess a viscosity of up to 100 mPa s, and are used, inter alia, for the hydrophobicization of mineral surfaces.

High-viscosity agents for hydrophobicizing mineral surfaces generally lead to poor penetration behavior of the active substance into the substrate, especially in the case of very compact substrates, such as concrete with a low w/c ratio. The w/c ratio indicates the ratio of water and cement; i.e., the greater the proportion of water, the greater the subsequent amount of pores in the concrete. Furthermore, active substances having a relatively high degree of oligomerization may result in the discoloration of the substrate surface, this discoloration being caused by the failure of higher oligomers to penetrate the substrate, or else the substrate surface is observed at least to have an unwanted sheen or an oily appearance.

EP 0 579 453 A2 teaches a process for preparing alkylalkoxysiloxanes, especially an isobutyltrimethoxysilane-based system, in which from 0.1 to 0.6 mol of water per mole of alkoxysilane is used for controlled hydrolysis. In this case, the products are alcohol-containing mixtures which include a high proportion of silane monomer, i.e., reactant, as a result of which the product on application has a high volatile monomer content and, furthermore, possesses a low flash point. Products of a low flash point are subject to strict transport and safety-at-work regulations in a number of countries, including the EU, Japan, and the USA.

J. Organometallic Chem. 489 (1995) teaches the hydrolysis of i-propyl- and, respectively, i- and n-butyltrimethoxysilane, in which a catalyst, such as dibutyltin laurate, and a solvent, such as tetrahydrofuran, are used.

WO 92/06101 discloses solvent-free organoalkoxysiloxanes having from 2 to 9 Si units for the water repellency treatment of mineral building materials, the repellency properties of the siloxane being enhanced if desired by the addition of organic fluorine compounds. The list of organic groups in the organoalkoxysiloxane includes $C_1$ to $C_{30}$ alkyl/cycloalkyl/arylalkyl/alkaryl or mixtures thereof, and also olefinic organic groups and organic groups substituted by heteroatoms and/or fluorine atoms. Particular emphasis is placed on organoalkoxysiloxanes with $C_{4-8}$-alkyl groups and possess a degree of oligomerization ranging from 2 to 4, with 1,3-di-n-octyl-1,1,3,3-tetraethoxy- and -methoxydisiloxane being highlighted in particular. It is complicated and expensive to conduct controlled preparation of such a disiloxane.

U.S. Pat. No. 5,543,173 discloses not only aminoalkyl- and diaminoalkyl-functional polysiloxanols, but also methyl-, ethyl-, 1-propyl- and n-butyl-functional, especially octyl-functional, polysiloxanols. These compounds are prepared by controlled hydrolysis of the corresponding alkoxysilanes, the product including a considerable fraction of alcohol produced by hydrolysis and significant amounts of solvent, such as toluene or methyl isobutyl ketone.

For the hydrophobicization of concrete, EP 0 101 816 B1 discloses the use of solvent-free $C_3$ to $C_8$ alkylalkoxysilanes, i.e., monomeric alkylalkoxysilanes.

Monomeric alkylalkoxysilanes, such as n-propyltriethoxysilane (PTEO), isobutyltriethoxysilane (IBTEO) and octyltriethoxysilane (OCTEO), for example, although they possess a comparatively good penetration behavior, are nevertheless hampered by the drawback that on the basis of their own vapor pressure, they may evaporate, leading to material losses and environmental pollution (VOCs—volatile organic compounds).

It is also known to apply $C_3$ to $C_8$ alkylalkoxysilanes in solution in an alcohol or in other evaporable or volatile solvents. Here again, marked evaporation losses are found. Furthermore, PTEO, IBTEO, and the solutions in highly volatile solvents possess a low flash point.

Furthermore, monomeric PTEO gives emulsions having a flash point below 55° C., and is therefore classified as a flammable liquid requiring appropriately complex storage, transport, and handling.

In order to lessen these drawbacks, particular use has been made in the past of alkoxysilanes of high molecular weight, i.e., alkylalkoxysilanes with an alkyl chain having a large number of carbon atoms, an example being octyltriethoxysilane. OCTEO is generally prepared by hydrosilylating octene with trichlorosilane and then esterifying the product, which is very complex to do. The product in this case carries a high price. n-Propyltrichlorosilane (PTS) is obtained as a byproduct in industrial processes. However, the quantity available on the market exceeds the demand for PTS and PTEO.

SUMMARY OF THE INVENTION

Accordingly, one object of the present invention is to provide a method of hydrophobicizing concrete and other mineral building materials, thereby resulting in a product which is secure against evaporation under standard conditions and which, in particular, possesses a higher flash point than PTEO or IBTEO, possesses good application properties, and is highly effective.

Another object of the present invention is to provide a compound based on PTS or PTEO which is sufficiently stable to hydrolysis.

Briefly, this object and other objects of the present invention as hereinafter will become more readily apparent can be attained by a specific oligomer mixture of n-propylethoxysiloxanes which contains from 90 to 100% by weight of n-propylethoxysiloxanes having a degree of oligomerization ranging from 2 to 6.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

the FIGURE shows the flash point of various alkylalkoxysilane emulsions as a function of the storage time (*storage temperature approx. 50±10° C.).

DETAILED DESCRIPTION OF THE PREFERRED EMBODIMENTS

The oligomer mixture of the invention is prepared by subjecting n-propyltrimethoxysilane or n-propyltrichlorosilane to controlled hydrolysis and condensation in ethanolic solution and in the presence of a hydrolysis and condensation catalyst, preferably in the presence of hydrogen chloride (HCl), with the addition of 0.65 to 0.85 mole of water per mole of Si, with thorough mixing, at a temperature in the range of 40 to 120° C., preferably in the range of 60 to 100° C., particularly preferably of 70 to 90° C., and most particularly preferably in the region of 80° C., wherein after a reaction time of 30 minutes to 24 hours, preferably after 3 to 6 hours, more particularly preferably after 4 hours, some or all of the alcohol, including volatile catalyst, is removed from the system. In general, mixtures of the invention obtained in this way contain ≦5% by weight of ethanol, preferably less than 2% by weight. Particularly preferably, the ethanol content ranges from 0.001 to less than 0.5% by weight, i.e., down to the detection limit. The remaining constituents of the concentrate are the oligomers of the invention.

The oligomer mixture of n-propylethoxysiloxanes of the invention is particularly noteworthy because of its exemplary economy, the surprising simplicity of its preparation and its stability, its advantageous and comparatively low viscosity, its good resistance to hydrolysis, and by the fact that it has a flash point of well above 60° C., i.e., based on the concentrate of the invention. Furthermore, the oligomer mixture of the invention is outstandingly suitable for the water repellency treatment of inorganic substrates, especially concrete and porous mineral facade materials. Moreover, the mixture of the invention possesses excellent application properties. When the oligomer mixture of the invention is applied or when an aqueous emulsion into which the oligomer mixture has been incorporated is applied, it is possible to achieve very good depths of penetration into concrete and therefore, simply and economically, an outstanding deep-down impregnation. Moreover, substrates treated in accordance with the invention generally exhibit no color changes. Furthermore, oligomer mixtures of the invention are generally secure against evaporation and possess outstanding storage stability, even in the case of emulsions in water; a 50% aqueous emulsion is usable after a period of one year. Additionally, the present oligomer mixture may advantageously be used together with monomeric organofunctional silanes and/or siloxanes.

n-Propylethoxysiloxanes may generally be described approximately, but illustratively, by the following formula:

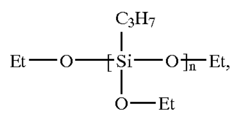

in which n indicates the degree of oligomerization. In other words, the degree of oligomerization indicates the number of Si units per molecule. In the investigation of the present invention, the methods used to determine the degree of oligomerization were gel permeation chromatography (GPC) and $^{29}$Si-NMR. When an oligomer mixture is stated as being, for example, 100% by weight, based on well-defined oligomers, this figure refers to the present detection limit (around 1%) of corresponding oligomers prepared by said methods. In order to be able to describe the siloxanes of the invention in more detail, the present specification refers to structures known as M, D and T structures. Regarding the nomenclature of such siloxane structures, reference may be made to "Römpp Chemielexikon" under the entry headed Silicone.

The present invention therefore provides an oligomer mixture of n-propylethoxysiloxanes containing from 80 to 100% by weight of n-propylethoxysiloxanes having a degree of oligomerization ranging from 2 to 6, preferably a degree of oligomerization ranging from 3 to 6. Preference is given to those oligomer mixtures of the invention containing from 90 to 100% by weight of n-propylethoxysiloxanes having a degree of oligomerization ranging from 2 to 6, in particular from 3 to 6. Particular preference is given to oligomer mixtures of the invention containing at least 95% by weight of n-propylethoxysiloxanes having a degree of oligomerization ranging from 2 to 6, in particular from 3 to 6.

Preferably, oligomer mixtures of the invention contain the following proportions of n-propylethoxysiloxanes, the amounts in each case adding up to 100% by weight by virtue of additional components, i.e., substantially, n-propylethoxysiloxanes:

from 0 to 30% by weight, with preferably less than 5% by weight, particularly preferably from 0.001 to less than 1% by weight, of n-propylethoxysiloxane having a degree of oligomerization n of 2 which possesses an $M_2$ structure;

from 10 to 40% by weight, preferably from 15 to 35% by weight, of n-propylethoxysiloxanes possessing an $M_2D$ and/or $D_3$ structure, the structures each corresponding to a molecular weight of an n-propylethoxysiloxane whose degree of oligomerization n is 3;

from 30 to 60% by weight, preferably from 35 to 50% by weight, particularly preferably from 35 to 45% by weight, of n-propylethoxysiloxanes possessing an $M_2D_2$ and/or $M_3T$ and/or $D_4$ structure, the structures each corresponding to a molecular weight of an n-propylethoxysiloxane whose degree of oligomerization n is 4;

from 5 to 30% by weight, preferably from 10 to 25% by weight, particularly preferably from 15 to 24% by weight, of n-propylethoxysiloxanes possessing an $M_2D_3$ and/or $M_3DT$ and/or $D_5$ structure, the structures each corresponding to a molecular weight of an n-propylethoxysiloxane whose degree of oligomerization n is 5;

from 0.1 to 25% by weight, preferably from 0.5 to 20% by weight, particularly preferably from 5 to 20% by weight, of n-propylethoxysiloxanes possessing an $M_2D_4$ and/or $M_3D_2T$ and/or $M_4T_2$ and/or $D_6$ structure, the structures each corresponding to a molecular weight of an n-propylethoxysiloxane whose degree of oligomerization n is 6.

If desired, the present oligomer mixture of n-propylethoxysiloxanes may contain less than 10% by weight, preferably from 0 to 8% by weight, more preferably from 0.001 to less than 5% by weight, of n-propylethoxysiloxanes having a degree of oligomerization of more than 6.

The present oligomer mixture suitably contains from 0 to less than 5% by weight of n-propylethoxysiloxanes having a degree of oligomerization n ranging from 7 to 20.

It is also suitable if the present oligomer mixture contains from 0 to less than 1% by weight of n-propylethoxysiloxanes having a degree of oligomerization n of more than 20.

Oligomer mixtures of n-propylethoxysiloxanes of the invention preferably contain, that is, insofar as can be detected, exclusively those n-propylethoxysiloxanes having a degree of oligomerization n ranging from 2 to 6, preferably only those where n ranges from 3 to 6.

Furthermore, the oligomer mixture of the invention may contain free ethanol in an amount ranging from 0 to less than 5% by weight, based on the overall mixture, preferably from 0.001 to less than 2% by weight, particularly preferably less than 1% by weight, of free ethanol.

Furthermore, oligomer mixtures of the invention have a viscosity preferably ranging from 3 to 20 mPa s, more preferably from 3 to 10 mPa s, particularly preferably from 4 to 8 mPa s, and most particularly a viscosity ranging from 4 to 7 mPa s. The viscosity is measured generally by the procedure described in DIN 53 015.

The present invention also provides a process for preparing an oligomer mixture of n-propylethoxysiloxanes, which comprises subjecting n-propyltriethoxysilane or n-propyltrichlorosilane to controlled hydrolysis and condensation in ethanolic solution and in the presence of a hydrolysis and condensation catalyst, preferably hydrogen chloride, with the addition of from 0.65 to 0.85 mol of water per mole of Si at a temperature in the range from 40 to 120° C., and, suitably after a reaction time of from 5 minutes to 24 hours, removing alcohol from the reaction system and, if appropriate, the volatile catalyst present, such as hydrogen chloride, for example.

The removal of the alcohol and of the hydrogen chloride (HCl) is done preferably by distillation under reduced pressure, because these techniques treat the product gently.

In accordance with the process of the invention, the oligomer mixture of the invention is obtained as a product mixture which may suitably be used as a concentrate, in dissolved form or as an emulsion, alone or in combination with other active substances.

The present invention likewise provides an oligomer mixture of n-propylethoxysiloxanes which is prepared by the process of the invention.

Furthermore, the present invention provides for the use of an oligomer mixture of n-propylethoxysiloxanes of the invention for the water-repelling (hydrophobicizing), oil-repelling (oleophobicizing), dirt-repelling, bioinfestation-preventing and/or corrosion-preventing treatment of inorganic surfaces. Oligomer mixtures of the invention may suitably be used for antigraffiti applications or in compositions for antigraffiti applications, especially in conjunction with organic fluorine compounds and/or fluorine functional silanes or siloxanes.

Oligomer mixtures of n-propylethoxysiloxanes of the invention are particularly suitable for use for the deep-down impregnation of building materials or structures, very particularly for mineral building materials, such as concrete, lime sandstone, granite, lime, marble, perlite, clinker, brick, porous tiles, terra cotta, natural stone, aerated concrete, fiber cement, prefabricated concrete components, mineral plaster, screed, clay articles, and also artificial stone, masonry, facades, roofs, and also structures, such as bridges, harbors, residential buildings, industrial buildings, and buildings used by the public, such as multistory car parks, railroad stations or schools, and also prefabricated parts, such as railroad ties or L-shaped blocks, to name but a few examples.

Moreover, the siloxane mixtures obtained in accordance with the invention may be used to hydrophobicize and surface-modify textiles, leather, cellulose products and starch products, to coat glass fibers and mineral fibers, as binders or as additives to binders, to surface-modify fillers, to improve the rheological properties of dispersions and emulsions, as adhesion promoters, for improving the adhesion of organic polymers to inorganic substrates, for example, as release agents, as crosslinkers, or as additives to paints and varnishes.

The present invention also provides for the use of an oligomer mixture of n-propylethoxysiloxanes of the invention to treat smooth, porous and/or particulate substrates, examples being powders, dusts, sands, fibers, flakes of organic or inorganic substrates, such as quartz, silica, including pyrogenic silica, minerals containing silicon oxide, titanium oxides and other oxygen-containing titanium minerals, aluminum oxide and other minerals containing it, aluminum hydroxides, such as aluminum trihydroxide, magnesium oxide and minerals containing it, magnesium hydroxides, such as magnesium dihydroxide, calcium carbonate and minerals containing it, glass fibers, mineral wool fibers, and also particular ceramic powders, such as silicon carbide, silicon nitride, boron carbide, boron nitride, aluminum nitride, tungsten carbide, metal or metal powders, especially aluminum, magnesium, silicon, copper, iron, and also metal alloys, and carbon blacks.

An oligomer mixture of the invention is suitably used in concentrated form, as a dilute alcoholic solution, or in solution in hydrocarbons. In particular, an oligomer mixture of the invention is employed in a concentration ranging from 0.1 to 100% by weight, preferably from 1 to 40% by weight, particular preferably from 20 to 40% by weight. Suitable examples of alcohols which may be used include methanol, ethanol, isopropanol, n-propanol, n-, 1- and t-butanol, preferably ethanol. Suitable examples of hydrocarbons that may be used include linear or branched aliphatic or aromatic systems containing 5 to 20 carbon atoms, such as pentane, hexane, cyclohexane, heptane, octane, decane, toluene, xylene, paraffins or white oils, preferably mineral spirits.

An embodiment of the present invention is the combination of the oligomer mixture of the invention together with at least one organoalkoxysilane selected from the group consisting of alkylsilanes, such as methyltrimethoxysilane, methyltriethoxysilane, ethyltrimethoxysilane, ethyltriethoxysilane, propyltrimethoxysilane, propyltriethoxysilane,—and i-butyltrimethoxysilane,—and i-butyltriethoxysilane,—and i-pentyltrimethoxysilane,—and i-pentyltriethoxysilane,—and i-hexyltrimethoxysilane,—and i-octyltrimethoxy silane,—and i-octyltriethoxysilane, hexadecyltrimethoxysilane, hexadecyltriethoxysilane, octadecyltrimethoxysilane, octadecyltriethoxysilane, dimethyldimethoxysilane, dimethyldiethoxysilane,—and i-butylmethyldimethoxysilane,—and i-butylmethyldiethoxysilane, cyclohexylmethyldimethoxysilane, diisopropyldimethoxysilane, diisobutyldimethoxysilane and isobutylisopropyldimethoxysilane, vinylsilanes, such vinyltrimethoxysilane, vinyltriethoxysilane and vinyltris(2-methoxyethoxysilane), aminoalkoxysilanes, such as 3-aminopropyltrimethoxysilane, 3-aminopropyltriethoxysilane, N-(n-butyl)-3-aminopropyltrimethoxysilane, 3-aminopropylmethyldiethoxysilane, 3-ureido propyltrimethoxysilane, 3-ureidopropyltriethoxysilane, N-aminoethyl-3-aminopropyltrimethoxysilane, N-aminoethyl-3-aminopropyltriethoxysilane, triamino-functional propyltrimethoxysilane and 3-(4,5-dihydroimidazolyl)propyltriethoxysilane, glycidyl ether-functional and glycidylalkyl-functional alkoxysilanes, such as 3-glycidyloxypropyltrimethoxysilane and 3-glycidyloxypropyltriethoxysilane, fluoroalkyl-functional alkoxysilanes, such as tridecafluorooctyltriethoxysilane and tridecafluorooctyltrimethoxysilane, acryloyl- or methacryloyl-functional alkoxysilanes, such as acryloyloxypropyltrimethoxysilane, acryloyloxypropyltriethoxysilane, 3-methacryloyloxypropyltrimethoxysilane, 3-methacryloyloxypropyltriethoxysilane, 3-methacryloyloxy-2-methylpropyltrimethoxysilane and 3-methacryloyloxy-2-methylpropyltriethoxysilane, mercapto-functional alkoxysilanes, such as mercaptopropyltrimethoxysilane and mercaptopropyltriethoxysilane, sulfane- or polysulfane-functional alkoxysilanes, such as bis(triethoxysilylpropyl)tetrasulfane, bis (trimethoxysilylpropyl)tetrasulfane, bis (triethoxysilylpropyl)disulfane, bis(trimethoxysilylpropyl) disulfane, bis(triethoxysilylpropyl)sulfane, bis (trimethoxysilylpropyl)sulfane, bis (triethoxysilylpropyl) pentasulfane and bis(trimethoxysilylpropyl)pentasulfane, it being possible for the organosiloxanes to be present in a concentration ranging from 0.5 to 99.5%, based on the composition, and/or at least one organosiloxane selected from the group consisting of vinyl-functional siloxanes, vinyl-alkyl-functional siloxanes (cocondensates), methacryloyl-functional siloxanes, amino-functional siloxanes, aminoalkyl alkyl-functional siloxanes, aminoalkyl-fluoroalkyl functional siloxanes or corresponding cocondensates and also condensates as described, for example, in

| | | |
|---|---|---|
| EP 0 590 270 A, | EP 0 748 357 A, | EP 0 814 110 A, |
| EP 0 879 842 A, | EP 0 846 715 A, | EP 0 930 342 A, |
| DE 198 18 923 A, | DE 198 34 990 A, | DE 198 49 308 A, |

DE 199 04 132 A and DE 199 08 636 A, and/or at least one silicic ester, examples being tetramethoxysilane, tetraethoxysilane, tetra-n-propyl silicates, tetrabutyl glycol silicates, and also ethyl polysilicates, and/or at least one oligomeric silicic ester, such as DYNASYLAN(® 40, or see also DE 27 44 726 C and also DE 28 09 871 C, in one formulation.

The oligomer mixture of the invention is suitably used in the presence of a hydrolysis and/or condensation catalyst. By this means it is possible to further improve the beading effect. Suitable examples of such hydrolysis and/or condensation catalysts include mineral acids, such as hydrogen chloride, sulfuric acid and nitric acid; organic acids, such as formic acid and acetic acid; titanates, such as tetrabutyl, tetrapropyl, tetraethyl titanate; zirconates, such as tetrabutyl, tetrapropyl and tetraethyl zirconates; organotin compounds, such as DBTL: i.e. dibutyltin laurate. The acid may be used, for example, in aqueous or dilute form, but also in concentrated form.

Oligomer mixtures of n-propylethoxysiloxanes of the invention are notable in particular for good stability with respect to hydrolysis, so that they may be used advantageously to formulate stable, aqueous emulsions having a high flash point.

The oligomer mixture of the invention is preferably suitable for use as an oil phase in an aqueous, low-viscosity to high-viscosity pastelike emulsion, as described for example in EP 0 538 555 A1. Accordingly, the oligomer mixture of the invention may be used together, for example, with emulsifiers, buffers, such as sodium carbonate, thickeners, biocides, especially fungicides and algicides, in an aqueous emulsion.

In particular, the oligomer mixture of the invention may also be used together with at least one water-dissolved silane cocondensate, as disclosed for example in DE 15 18 551 A, EP0 587 667A, EP0 716 127 A, EP0 716 128 A, EP0 832 911 A, EP0 846 717 A, EP 0 846 716 A, EP 0 885 895 A, DE 198 23 390 A and DE 199 55 047 A, and/or at least one insoluble or water-soluble organic fluorine compound, as disclosed in U.S. Pat. Nos. 5,112,393, 3,354,022 or WO 92/06101, and/or a water-emulsified silicone wax.

The present invention additionally provides formulations or compositions advantageously comprising an oligomer mixture of the invention; in other words, an oligomer mixture of the invention is used per se or as a starting component in the preparation of a formulation or composition.

Another aspect of the invention is a method of treating substrates by applying a composition or formulation of the invention to a substrate surface and subjecting it, if desired, to thermal and/or photochemical after treatment, by IR or UV exposure, for example.

Still another aspect of the invention is a layer that is prepared, for example, by coating the present composition or formulation on a substrate, or by impregnation of a substrate with the composition or formulation of the invention.

Yet another aspect of the invention are surface-treated substrates that are prepared in an advantageous, inventive manner. Examples are concrete, lime sandstone, clinker, brick, terra cotta, artificial stone, natural stone, aerated concrete, fiber cement, and clay articles treated with the composition or formulation of the invention.

Another embodiment of the invention is articles based on a substrate which has been surface-treated in accordance with the invention. Examples of such articles are prefabricated concrete parts, such as prefabricated houses, tunnels, bridges, and containers which are impregnated with the composition of the invention.

In general, the oligomer mixture of the invention may be prepared as follows:

n-Propyltriethoxysilane may be prepared from n-propyltrichlorosilane with ethanol by complete esterification with elimination and removal of HCl, as is known per se. Subsequently, the partial hydrolysis of the ester is conducted. In general, the reaction takes place with the addition of appropriate catalysts, e.g. HCl. Suitably, the reaction is conducted in dilute solution. Ethanol in excess may be used for this purpose. For the hydrolysis it is preferred to employ specifically from 0.65 to 0.85 mol of water per mole of n-propyltriethoxysilane. The hydrolysis takes place preferably at an elevated temperature, usually in the range from 40 to 120° C., and is generally conducted such that all of the water reacts. The alcohol produced by hydrolysis may be suitably removed from the reaction mixture by distillation, together with the volatile catalyst. In general, this distillation is conducted at an elevated temperature, usually from 40 to 180° C., and under vacuum, usually <10 mbar abs. To complete the work-up by distillation, a stream of inert gas may be used as an entrainer; preferably, dry nitrogen is used for this purpose. The colorless, neutral bottom product may be used directly without further work-up as an architectural preservative or as an oil phase for aqueous emulsion systems, or may be utilized for the other applications mentioned.

Alternatively, the n-propylalkoxysiloxane may be synthesized directly from n-propyltrichlorosilane, water and ethanol. Again, from 0.65 to 0.85 mol of water per mole of n-propyltrichlorosilane used is employed for the hydrolysis reaction. Advantageously, the water is mixed together with ethanol, the mixture is added to the n-propyltrichlorosilane, and the reaction is conducted, with ethanol preferably being used in an excess amount relative to the stoichiometry of the reaction. Suitably, HCl is removed from the reaction container. The reaction takes place preferably at an elevated temperature; see above. Residual HCl may be removed by adding additional ethanol and conducting distillation at an elevated temperature under vacuum. Alternatively, a base, such as sodium ethoxide or ammonia, for example, may be used for the neutralization, i.e., the reaction and removal of HCl from the reaction mixture. Normally, the corresponding salt, sodium chloride or ammonium chloride, respectively, precipitates, and can be removed from the reaction mixture by filtration.

The procedures described above produce a product of the invention which has, for example, the following physico-chemical properties and the following oligomer distribution:

| | |
|---|---|
| Flash point: | 118° C. |
| Boiling point: | 268° C. |
| viscosity: | 4.5 mPa s |
| Water content: | ≦0.05% |
| Free ethanol: | ≦0.1% |

| Degree of oligomerization (structural types) | Proportion in % by weight |
|---|---|
| 3 ($M_2D$, $D_3$) | 32 |
| 4 ($M_2D_2$, $M_3T$, $D_4$) | 43 |
| 5 ($M_2D_3$, $M_3DT$, $D_5$) | 15 |
| 6 ($M_2D_4$, $M_3D_2T$, $M_4T_2$, $D_6$) | 5 |

FIG. 1 shows the flash point properties of various emulsions as a function of the storage time.

FIG. 1 accordingly indicates the flash points of monomeric n-propyltriethoxysilane (50% by weight PTEO in water), monomeric 1-butyltriethoxysilane (50% by weight IBTEO in water), monomeric n-octyltriethoxysilane (WS 405, 50% by weight OCTEO in water) and experimental product 9892 (50% by weight n-propylethoxysiloxane in water); cf. Example 1. Products whose flash points are lower than 55° C. require labeling under German chemical law. The graph shows that, as the storage time at elevated temperature (40° C.) increases, the flash point as a result of free hydrolysis alcohol decreases. The inventive product VPS 9892 and the OCTEO-based WS 405 have virtually identical flash point properties; however, the product of the invention, based on PTEO condensate, is much less expensive. Moreover, it should be noted that the emulsions of PTEO and IBTEO are unstable in that severe creaming occurs after just one day. Emulsions of this kind cannot be used for architectural preservation applications. In this case, each of the flash point determinations is made after intensive homogenization.

Having now generally described this invention, a further understanding can be obtained by reference to certain specific examples which are provided herein for purposes of illustration only and are not intended to be limiting unless otherwise specified.

EXAMPLES

Example 1

Preparation of a Mixture of Oligomeric n-propylsiloxanes From n-propyltriethoxysilane and Water (0.8 mol of Water per Mole of Si) Product Designation VPS 9892

A 2 liter jacketed stirring apparatus is charged with n-propyltriethoxysilane (PTEO) and this initial charge is heated to approximately 80° C. At this temperature, a mixture of ethanol, water and hydrochloric acid is added dropwise by a dropping funnel. The entire reaction mixture is subsequently boiled at reflux for four hours. Thereafter, the ethanol used and the ethanol released during the hydrolysis are removed by distillation, first at ambient pressure and then in vacuo. The liquid remaining at the bottom is VPS 9892.

| Amounts used: | |
|---|---|
| PTEO | 1,120.5 g |
| Water | 76.5 g |
| Ethanol | 321 g |
| HCl (32% by weight in water) | 1.5 g |
| Product isolated: | |
| VPS 9892 (yield: 97% of theory) | 780.81 g |

Example 2

Preparation of a Mixture of Oligomeric n-propylsiloxanes (Hydrolyzed With 0.6 Mol of Water Per Mole of Si)

A 4 literjacketed stirring apparatus is charged with n-propyltriethoxysilane (PTEO) and this initial charge is heated to approximately 80° C. At this temperature, a mixture of ethanol, water and hydrochloric acid is added dropwise by a dropping funnel. The entire reaction mixture is subsequently boiled at reflux for four hours. Thereafter, the ethanol used and the ethanol released during the hydrolysis are removed by distillation, first at ambient pressure and then in vacuo. The liquid remaining at the bottom is the desired propylsiloxane.

| Amounts used: | |
|---|---|
| PTEO | 1,442.7 g |
| Water | 75.6 g |
| Ethanol | 1,518 g |
| HCl (32% by weight in water) | 1.58 g |

-continued

| Product isolated: | |
|---|---|
| Propylsiloxane (yield: 91% of theory) | 1,030.9 g |

Composition by GPC (gel permeation chromatography). By means of GPC, mixtures of different molecular size can be separated. By comparison with a standard, it is possible to determine the individual molecular weights:

| | |
|---|---|
| Monomer | 5% |
| M2 | 63% |
| M2D, D3 | 27% |
| M2D2, M3T, D4 | 3% |
| M2D3, M3DT, D5 and higher oligomers | 2% |
| Viscosity | 2.8 MPa s (DIN 53 015) |
| Flash point | 97° C. (EN 22719) |

Comparative Example A

Preparation of a Mixture of Oligomeric Propylsiloxanes (Hydrolyzed With 1.6 Mol of Water Per Mole of Si)

A 4 liter jacketed stirring apparatus is charged with n-propyltriethoxysilane (PTEO) and this initial charge is heated to approximately 80° C. At this temperature, a mixture of ethanol, water and hydrochloric acid is added dropwise by a dropping funnel. The entire reaction mixture is subsequently boiled at reflux for four hours. Thereafter, the ethanol used in the reaction and the ethanol released during the hydrolysis are removed by distillation, first at ambient pressure and then in vacuo. The liquid remaining at the bottom is the desired propylsiloxane.

The analysis of the alcohol removed by distillation showed a significant water content, reducing the amount of water effectively used to a FIGURE of approximately 1.33 mol of water per mole of Si employed.

| Amounts used: | |
|---|---|
| PTEO | 2,473.2 g |
| Water | 345.9 g |
| Ethanol | 593.6 g |
| HCl (32% by weight in water) | 2.34 g |
| Product isolated: | |
| Propylsiloxane (yield: 95% of theory) | 1,222 g |
| Composition by GPC: | |
| M2: | 0% |
| M2D, D3: | 0% |
| M2D2, M3T, D4: | 8% |
| M2D3, M3DT, D5: | 8% |
| M2D4, M2D2T, M4T2, D6: | 14% |
| Higher oligomers | 70% |
| Viscosity | 165 MPa s (DIN 53 015) |
| Flash point | 136° C. (EN 22719) |

Example 4

Penetration Behavior of VPS 9892 on Lime Sandstone

A lime sandstone specimen (sawn, commercially customary lime sandstone in blocks 5×5×5 cm, dried in a forced-air drying cabinet at 60° C. to constant weight and then cooled to room temperature in a laboratory for about 3 hours) is immersed in VPS 9892 for 2×5 seconds. Between the impregnating steps, the specimen is allowed to drip-dry for 30 seconds. Following the second impregnation, excess impregnant is dabbed off with an absorbent cloth. Subsequently, the test specimen is left to react at room temperature for about 1 week in the laboratory. Thereafter, the test specimen is split into 2 halves using a hammer and chisel. The fresh fracture surfaces are treated with an aqueous dye solution (Azorubin S). Hydrophilic regions are stained red, hydrophobic regions remain colorless, since they are not wetted by the aqueous ink. The uncolored regions show the depth of penetration. This is measured at different regions by means of an appropriate scale, and the mean is formed. In the case of the test specimens treated with VPS 9892, the averaged penetration depth is 5 mm and is therefore sufficient for permanent hydrophobicization. Penetration depths of less than 1 mm point to an inadequate hydrophobicizing effect. The specimens impregnated with VPS 9892 show no visually perceptible surface change. Following reaction (1 week, laboratory), the surface is tack-free. VPS 9892 is therefore outstandingly suitable for the hydrophobicizing impregnation of porous mineral building materials.

Comparative Example B

Penetration Behavior of an Octylsiloxane Mixture According to the Example of EP 0 814 110 A1 on Lime Sandstone A lime sandstone specimen (sawn, commercially customary lime sandstone in blocks 5×5×5 cm, dried in a forced-air drying cabinet at 60° C. to constant weight and then cooled to room temperature in a laboratory for about 3 hours) is immersed in an octylsiloxane in accordance with the example of EP 0 814 110 A for 2×5 seconds. Between the impregnating steps, the specimen is allowed to drip-dry for 30 seconds. Following the second impregnation, excess impregnant is dabbed off with an absorbent cloth. Subsequently, the test specimen is allowed to react at room temperature for about 1 week in the laboratory. Thereafter, the test specimen is split into 2 halves using a hammer and chisel. The fresh fracture surfaces are treated with an aqueous dye solution (Azorubin S). Hydrophilic regions are stained red, hydrophobic regions remain colorless, since they are not wetted by the aqueous ink. The uncolored regions show the depth of penetration. This is measured at different regions by means of an appropriate scale, and the mean is formed. In the case of the test specimens treated with octylsiloxane in accordance with the example of EP 0 814 110 A, the averaged penetration depth is <1 mm and is therefore insufficient for permanent hydrophobicization. Penetration depths of less than 1 mm point to an inadequate hydrophobicizing effect. The specimens impregnated with octylsiloxane in accordance with the example of EP 0 814 110 A show a slight but distinctly perceptible surface darkening. This is undesirable for hydrophobicizing impregnations. Following reaction (1 week, laboratory), the surface is tack-free. A product of this kind is of only very limited suitability for the hydrophobicizing impregnation of porous mineral building materials.

Comparative Example C

Penetration Behavior of an Oligomeric n-propylsiloxane Mixture (Hydrolyzed With 1.6 Mol of Water Per Mole of Si) on Lime Sandstone A lime sandstone specimen (sawn, commercially customary lime sandstone in blocks 5×5×5 cm, dried in a forced-air drying cabinet at 60° C. to constant weight and then cooled to room temperature in a laboratory for about 3 hours) is immersed in an oligomeric propylsiloxane hydrolyzed with 1.6 mol of water per mole of Si for 2×5 seconds. Between the impregnating steps, the specimen is allowed to drip-dry for 30 seconds. Following the second impregnation, excess impregnant is dabbed off with an absorbent cloth. Thereafter, the test specimen is split into 2 halves using a hammer and chisel. The fresh fracture surfaces are treated with an aqueous dye solution (Azorubin S). Hydrophilic regions are stained red, while the hydrophobic regions remain colorless, because they are not wetted by the aqueous ink. The uncolored regions show the depth of penetration. This is measured at different regions by means of an appropriate scale, and the mean is formed. In the case of the test specimens treated with oligomeric propylsiloxane hydrolyzed with 1.6 mol of water per mole of Si the averaged penetration depth is <1 mm and is therefore insufficient for permanent hydrophobicization. Penetration depths of less than 1 mm point to an inadequate hydrophobicizing effect.

The specimens impregnated with oligomeric propylsiloxane hydrolyzed with 1.6 mol of water per mole of Si show a distinctly perceptible surface darkening. This is undesirable for hydrophobicizing impregnations. Following reaction (1 week, laboratory), the surface is not tack-free. A product of this kind is unsuitable for the hydrophobicizing impregnation of porous mineral building materials.

The disclosure of German priority application Serial Number 10056344.9 filed Nov. 14, 2000 is hereby incorporated by reference into the present application.

Obviously, numerous modifications and variations of the present invention are possible in light of the above teachings. It is therefore to be understood that within the scope of the appended claims, the invention may be practiced otherwise than as specifically described herein.

What is claimed is:

1. An oligomer of n-propylethoxysiloxanes, comprising from 90 to 100% by weight of n-propylethoxysiloxanes having a degree of oligomerization ranging from 3 to 6.

2. The oligomer mixture as claimed in claim 1 comprising at least 95% by weight of n-propylethoxysiloxanes having a degree of oligomerization ranging from 3 to 6.

3. The oligomer mixture as claimed in claim 1, comprising from 10 to 40% by weight of n-propylethoxysiloxanes possessing an $M_2D$ and/or $D_3$ structure.

4. The oligomer mixture as claimed in claim 1, comprising from 30 to 60% by weight of n-propylethoxysiloxanes possessing an $M_2D_2$ and/or $M_3T$ and/or $D_4$ structure.

5. The oligomer mixture as claimed in claim 1, comprising from 5 to 30% by weight of n-propylethoxysiloxanes possessing an $M_2D_3$ and/or $M_3DT$ and/or $D_5$ structure.

6. The oligomer mixture as claimed in claim 1, comprising from 0.1 to 25% by weight of n-propylethoxysiloxanes possessing an $M_2D_4$ and/or $M_3D_2T$ and/or $M_4T_2$ and/or $D_3$ structure.

7. The oligomer mixture as claimed in claim 1, comprising less than 10% by weight of n-propylethoxysiloxanes having a degree of oligomerizeration n of more than 6.

8. The oligomer mixture as claimed in claim 7, comprising less than 5% by weight of n-propylethoxysiloxanes having a degree of oligomerization n of from 7 to 20.

9. The oligomer mixture as claimed in claim 7, comprising less than 1% by weight of n-propylethoxysiloxanes having a degree of oligomerization n of more than 20.

10. The oligomer mixture as claimed in claim 1, comprising ≦5% by weight of free ethanol.

11. The oligomer mixture as claimed in claim 1, having a viscosity of from 3 to 20 mPa s.

12. A process for preparing an oligomer mixture of n-propylethoxysiloxanes as claimed in claim 1, which comprises:

subjecting n-propyltriethoxysilane or n-propyltrichlorosilane to hydrolysis and condensation in ethanolic solution and in the presence of a hydrolysis and condensation catalyst, with the addition of from 0.65 to 0.85 mol of water per mole of Si at a temperature in the range from 40 to 120° C.; and removing the alcohol and hydrogen chloride from the reaction system.

13. An oligomer mixture of n-propylethoxysiloxanes according to claim 1, which is prepared by the process of claim 12.

14. A method of repelling water, oil or dirt or preventing bioinfestation and/or corrosion of inorganic surfaces, comprising:

treating the surfaces of inorganic substrates with the oligomer mixture as claimed in claim 1.

15. The method as claimed in claim 14, wherein building materials or structures are impregnated with said oligomer mixture.

16. A method of treating smooth, porous and/or particulate substrates, comprising: treating said substrates with the oligomer mixture as claimed in claim 1.

17. A method of treating inorganic surfaces, comprising:

treating the surfaces of metal, ceramic, building materials and structures of iron, steel, brick, masonry, natural stone, concrete, lime sandstone, marble, tiles, artificial stone, sheet glass, hollow glass, laminated glass, bridges, roofs an facades with the oligomer mixture of claim 1, thereby providing water-, oil-, dirt- and/or paint-repellent properties or corrosion-prevention or adhesion-promoting treatment of the surfaces.

18. A method of hydrophobicizing materials, comprising:

treating textiles, leather, cellulose products and starch products with the oligomer mixture of claim 1, thereby hydrophobicizing and surface-modifying said products.

19. A method of coating, comprising:

coating glass fibers and mineral fibers with the oligomer mixture of claim 1.

20. A binder, comprising the oligomer mixture of claim 1 alone or in combination with other binder ingredients.

21. A method of surface-modifying fillers, comprising: treating fillers with the oligomer mixture of claim 1.

22. A method of improving the rheological properties of dispersions and emulsions, comprising:

incorporating the oligomer mixture of claim 1 in dispersions and emulsions.

23. A method of improving the adhesion of organic polymers on inorganic substrates, comprising:

adhering the polymer and inorganic substrate in the presence of the oligomer mixture of claim 1.

24. A release agent, comprising the oligomer mixture of claim 1.

25. Across-linking agent, comprising the oligomer mixture of claim 1.

26. A paint or varnish, comprising the oligomer mixture of claim 1 as an additive.

27. The oligomer mixture as claimed in claim 1 in the form of a concentrate, a dilute alcoholic solution or a solution in hydrocarbons for application.

28. The oligomer mixture as claimed in claim 1 combined with a hydrolysis and/or condensation catalyst.

29. A method of treating substrates, which comprises applying a composition or formulation as claimed in claim 1 to a substrate surface and optionally subjecting it to thermal and or photochemical after treatment.

30. A layer on a substrate or an impregnation of a substrate prepared as described in claim 29.

31. A surface-treated substrate prepared as claimed in claim 29.

32. An article prepared from a surface-treated substrate as claimed in claim 30.

33. An article prepared from a surface-treated substrate as claimed in claim 31.

34. A composition, comprising an oligomer mixture comprising from 80 to 100% by weight of n-propylethoxysiloxanes having a degree of oligomerization ranging from 2 to 6, together with (i) at least one organoalkoxysilane selected from the group consisting of alkyl-, vinyl-, aminoorganoalkoxysilanes, glycidyl ether-functional and glycidyloxyalkyl-functional alkoxysilanes, fluoroorgano-functional alkoxysilanes, acryloyl- or methacryloyl-functional alkoxysilanes, mercapto-functional alkoxysilanes, sulfane- or polysulfane-functional alkoxysilanes and/or (ii) at least one organosiloxane selected from the group consisting of vinyl-functional siloxanes, glycidyloxyalkyl-functional siloxanes, alkylfunctional siloxanes, methacryloyl-functional siloxanes, fluoroalkyl- and fluoroorgano functional siloxanes, and also corresponding cocondensates and/or (iii) at least one silicic ester and/or (iv) at least one oligomeric silicic ester.

35. An emulsion, comprising an oligomer mixture comprising from 80 to 100% by weight of n-propylethoxysiloxanes having a degree of oligomerization ranging from 2 to 6, as the oil phase in an aqueous emulsion.

36. A composition, comprising an oligomer mixture comprising from 80 to 100% by weight of n-propylethoxysiloxanes having a degree of oligomerization ranging from 2 to 6, together with at least one water-dissolved silane cocondensate and/or at least one water-soluble organic fluorine compound and/or at least one water-emulsified silicone wax.

* * * * *